United States Patent [19]

Frickel et al.

[11] 4,267,187
[45] May 12, 1981

[54] AMINOPROPANOL DERIVATIVES OF 2-(0-HYDROXYPHENYL)-PYRROLE

[75] Inventors: Fritz-Frieder Frickel, Ludwigshafen; Albrecht Franke, Wachenheim; Horst Koenig; Hans-Dieter Lenke, both of Ludwigshafen; Josef Gries, Wachenheim, all of Fed. Rep. of Germany

[73] Assignee: BASF Aktiengesellschaft, Fed. Rep. of Germany

[21] Appl. No.: 64,907

[22] Filed: Aug. 8, 1979

[30] Foreign Application Priority Data

Aug. 12, 1978 [DE] Fed. Rep. of Germany ....... 2835438

[51] Int. Cl.³ .................... A61K 31/40; C01D 207/30
[52] U.S. Cl. ............................ 424/274; 260/326.5 L
[58] Field of Search ................. 260/326.5 L; 424/274

[56] References Cited
PUBLICATIONS

Dollery et al. Clinical Pharm. & Therapeutics, 10, (1969), No. 6, pp. 765-799.

Primary Examiner—Donald G. Daus
Assistant Examiner—D. B. Springer

Attorney, Agent, or Firm—Keil & Witherspoon

[57] ABSTRACT

Alkylaminopropanol derivatives of 2-(o-hydroxyphenyl)-pyrrole of the formula (I)

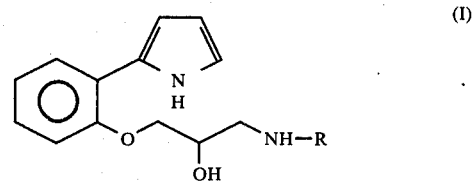

where R is hydrogen or is alkyl of 1 to 8 carbon atoms which is unsubstituted or substituted by hydroxyl, alkoxy of 1 to 3 carbons atoms or cycloalkyl of 3 to 8 carbon atoms in the ring, or is alkenyl or alkynyl of 2 to 8 carbon atoms or is cycloalkyl or cycloalkenyl of 3 to 8 carbon atoms in the ring, the cycloalkyl rings being unsubstituted or monosubstituted or disubstituted by alkyl or 1 to 3 carbon atoms, and their physiologically acceptable acid addition salts, processes for their preparation, and pharmaceutical formulations which contain the said compounds and may be used in the treatment of cardiac and circulatory disorders.

6 Claims, No Drawings

AMINOPROPANOL DERIVATIVES OF 2-(O-HYDROXYPHENYL)-PYRROLE

The present invention relates to aminopropanol derivatives of 2-(o-hydroxyphenyl)-pyrrole and their acid addition salts, their preparation and pharmaceutical formulations which contain these compounds and may be used in the treatment of cardiac and circulatory disorders.

We have found that compounds of the general formula (I)

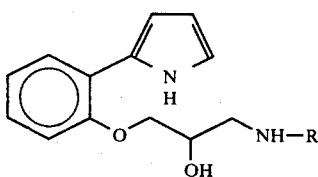

(I)

where R is hydrogen, alkyl of 1 to 8 carbon atoms which is unsubstituted or substituted by hydroxyl, alkoxy of 1 to 3 carbon atoms or cycloalkyl of 3 to 8 carbon atoms in the ring, or is alkenyl or alkynyl of 2 to 8 carbon atoms or is cycloalkyl or cycloalkenyl of 3 to 8 carbon atoms in the ring, the cycloalkyl rings being unsubstituted or monosubstituted or disubstituted by alkyl of 1 to 3 carbon atoms, and their acid addition salts, exhibit valuable pharmacological properties.

Examples of straight-chain or branched alkyl of 1 to 8 carbon atoms are methyl, ethyl, propyl, isoproyl, n-butyl, isobutyl, sec.-butyl, tert.-butyl, pent-2-yl, 2-nmethyl-but-2-yl, 3-methylbut-2-yl, 3-methyl-pent-3-yl, 2,3-dimethyl-but-2-yl, 3-ethyl-pent-3-yl, 2,3-dimethyl-pent-3-yl and 2,4,4-trimethyl-pentyl, and examples of substituted alkyl are 1-methoxy-prop-2-yl, 2-hydroxyeth-1-yl, 1-hydroxybut-2-yl, 3-hydroxy-3-methyl-but-1-yl and 1-cyclopropyleth-1-yl.

Amongst the alkyl radicals, those which are of 3 to 6 carbon atoms and are branched at the carbon atom in the α-position of the amino nitrogen are preferred. Accordingly, preferred alkyl radicals are isopropyl, tert.-butyl, 2-methyl-but-2-yl, but-2-yl, 3-methylpent-3-yl and pent-2-yl. Appropriate substituents for the preferred alkyl radicals are, in particular, alkoxy of 1 to 3 carbon atoms, especially methoxy, such a substituted alkyl radical being, for example, 1-methoxy-prop-2-yl.

Examples of alkenyl or alkynyl of 2 to 8 carbon atoms are prop-1-en-3-yl, but-3-yn-2-yl, 2-methyl-but-3-yn-2-yl and 3-ethyl-pent-1-yn-3-yl. Amongst these, alkynyl of 3 to 6 carbon atoms, eg. but-3-yn-2-yl and 2-methyl-but-3-yn-2-yl, are preferred.

Examples of cycloalkyl are cyclopropyl, cyclobutyl, cyclopentyl and cycloheptyl, amongst which cyclopropyl is preferred. The preferred alkyl substituent of the said cyclic radicals is methyl, an example of a substituted radical being dimethylcyclohexyl.

In addition to the compounds mentioned in the Examples, the following illustrate the compounds according to the invention: 2-[2-[3-(2-methyl-butyl-2-amino)-2-hydroxypropoxy]-phenyl]-pyrrole, 2-[2-[3-(3-methyl-pentyl-3-amino)-2-hydroxypropoxy]-phenyl]-pyrrole, 2-[2-[3-(2,3-dimethyl-butyl-2-amino)-2-hydroxypropoxy]-phenyl]-pyrrole, 2-[2-(3-cycloheptylamino-2-hydroxypropoxy)-phenyl]-pyrrole, 2-[2-[3-(1-thiomethyl-2-methyl-propyl-2-amino)-2-hydroxypropoxy]-phenyl]-pyrrole, 2-[2-[3-(1-methoxy-propyl-2-amino)-2-hydroxypropoxy]-phenyl]-pyrrole, 2-[2-[3-(1-propen-3-amino)-2-hydroxypropoxy]-phenyl]-pyrrole and 2-[2-[3-(2-hydroxy-ethylamino)-2-hydroxypropoxy]-phenyl]-pyrrole.

The compounds according to the invention are prepared by reacting an aryl-substituted pyrrole of the general formula (II).

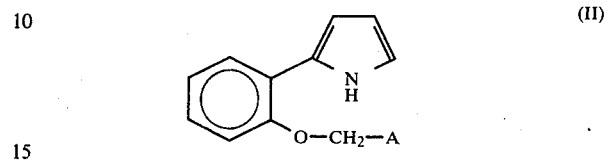

(II)

where A is

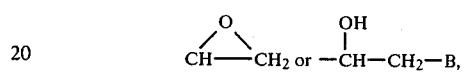

B being a nucleofugic leaving group, with an amine of the general formula $H_2N—R$ where R has one of the above meanings, in the conventional manner, advantageously in a solvent, and in the presence or absence of an acid-binding agent; the resulting compound may then be converted to a physiologically acceptable acid addition salt.

The leaving group B is preferably halogen, especially chlorine, bromine or iodine. Further examples of nucleofugic leaving groups are aromatic or aliphatic sulfonic acid ester groups, eg. the p-toluenesulfonic acid, p-bromobenzenesulfonic acid and methanesulfonic acid radical.

The reactions are carried out at room temperature or at elevated temperatures, advantageously at from 50° to 120° C. The reactions may be carried out under atmospheric pressure or in a closed vessel under superatmospheric pressure, with or without heating to the stated temperature range.

The starting compounds may be reacted directly, ie. without addition of a diluent or solvent. However, it is advantageous to carry out the reactions in the presence of an inert diluent or solvent, for example a lower alcohol of 1 to 4 carbon atoms, eg. methanol, ethanol or propanol, preferably isopropanol or ethanol, a lower saturated dialkyl ether, a dialkyl glycol ether or a cyclic ether, eg. diethyl ether, 1,2-dimethoxyethane, tetrahydrofuran or dioxane, benzene or an alkylbenzene, eg. toluene or xylene, an aliphatic hydrocarbon, eg. hexane, heptane or octane, a lower aliphatic ketone, eg. acetone, methyl ethyl ketone or methyl isobutyl ketone, a dialkylformamide, eg. dimethylformamide or diethylformamide, or dimethylsulfoxide, or in the presence of water or of a mixture of the said solvents.

The amine of the formula $H_2N—R$, used in excess, may also at times serve as a diluent or solvent.

Preferred solvents for the reaction of 2-[2-(2,3-epoxypropoxy)-phenyl]-pyrrole with an amine $R—NH_2$ are lower alcohols, especially ethanol or isopropanol, in which case the reaction is preferably carried out at from 50° to 100° C. and under atmospheric pressure. In the case of the nucleophilic replacement of the radical B, advantageous solvents to use are a lower aliphatic ketone, eg. acetone, methyl ethyl ketone or methyl isobutyl ketone, a cyclic ether, especially tetrahydrofuran or dioxane, or a dialkylformamide, eg. dimethylformamide, and the reaction is advantageously carried out at from 90° to 120° C. The reaction may or may not be carried out in the presence of a catalytic amount of sodium iodide or potassium iodide.

It should be mentioned that a mixture of the epoxide with a halohydrin may, where appropriate, also be used as the starting compound of the formula (II), since such mixtures can under certain circumstances be formed when the starting compounds of the formula (II) are prepared industrially.

In an advantageous embodiment of the nucleophilic replacement of the radical B by the amine used, the reaction is carried out in the presence of a base as the acid-binding agent. Preferred bases are alkali metal hydroxides, carbonates, bicarbonates or alcoholates, or tertiary organic amines, eg. pyridine or a trialkylamine, eg. trimethylamine or triethylamine. Amongst the alkali metal compounds, those of sodium and potassium are particularly suitable. The base is employed in the stoichiometric amount or in slight excess. At times it is advantageous to use an excess of the amine $H_2N-R$, employed in the reaction, also as the acid-binding agent.

The rate of reaction depends on the reaction temperature and the reaction is in general complete within 2–15 hours. The reaction product can be isolated in the conventional manner, for example by filtering off, or by distilling the diluent or solvent from the reaction mixture. The compound obtained is purified in the conventional manner, for example by recrystallization from a solvent, conversion to an acid addition compound, or column chromatography.

The starting compounds of the formula (II) may be obtained by alkylating 2-(o-hydroxyphenyl)-pyrrole with an epihalohydrin or an $\alpha,\omega$-dihalo-2-propanol. Suitable epihalohydrins are epichlorohydrin, epibromohydrin and epiiodohydrin, and suitable $\alpha,\omega$-dihalo-propan-2-ols are, in particular, 1,3-dichloro-propan-2-ol and 1,3-dibromo-propan-2-ol.

The reactions of 2-(o-hydroxyphenyl)-pyrrole, in order to prepare a starting compound of the formula (II), are advantageously carried out at from 0° to 120° C. under atmospheric pressure, or in a closed vessel under superatmospheric pressure. Advantageously, the reactions are carried out in an inert diluent or solvent, for example a lower aliphatic ketone, eg. acetone, methyl ethyl ketone or methyl isobutyl ketone, a lower alcohol of 1 to 4 carbon atoms, eg. methanol, ethanol, propanol or butanol, an aliphatic or cyclic ether, eg. a dialkyl ether, tetrahydrofuran or dioxane, a dialkylformamide, eg. dimethylformamide or diethylformamide, or dimethylsulfoxide or hexamethylphosphorotriamide, or in an excess of the alkylating agent as the diluent or solvent.

The reactions are preferably carried out in the presence of a base as the acid-binding agent. Suitable bases are alkali metal carbonates, bicarbonates, hydroxides, hydrides or alcoholates, especially of sodium and potassium, basic oxides, eg. aluminum oxide or calcium oxide, and organic tertiary bases, eg. pyridine, or lower trialkylamines, eg. trimethylamine or triethylamine. The bases may be employed in a catalytic amount, or in the stoichiometric amount, or in slight excess, relative to the alkylating agent used.

Preferably, 2-(o-hydroxyphenyl)-pyrrole is reacted with epibromohydrin or 1,2-dibromopropan-2-ol in a solvent mixture of an ether and a polar aprotic solvent, especially tetrahydrofuran or hexamethylphosphorotriamide, or a ketone, eg. acetone, at from 0° to 50° C.

According to a further method, the compounds of the general formula (I) are prepared by alkylating 2-(o-hydroxyphenyl)-pyrrole with a compound of the general formula (III) or (IV)

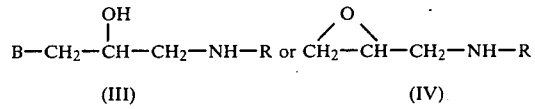

where B and R have the above meanings, in the conventional manner, advantageously in the presence of a solvent, and in the presence or absence of an acid-binding agent, at from 40° to 120° C. This reaction can for example be carried out in accordance with the conditions described in Swiss Pat. No. 451,115 or in German Laid-Open Application DOS No. 2,007,751.

The alkylation of 2-(o-hydroxyphenyl)-pyrrole with a compound of the formula (III) is preferably carried out in the presence of an acid-binding agent, such as an alkali metal hydroxide, carbonate, bicarbonate or alcoholate, or of a tertiary organic amine, preferably pyridine or a tertiary aliphatic amine, eg. trimethylamine or triethylamine. Amongst the alkali metal compounds, those of sodium and potassium are particularly suitable. The base is used in the stoichiometric amount or in slight excess.

Alternatively, the starting compound can be employed in the form of the alkali metal salt, such as the sodium salt or potassium salt.

The alkylation may also be carried out in the presence of a catalytic amount of an amine.

Advantageously, the alkylation reactions are carried out in an inert diluent or solvent, for example a lower aliphatic alcohol of 1 to 4 carbon atoms, eg. methanol, ethanol, propanol, isopropanol or a butanol, or a lower aliphatic ketone, eg. acetone, methyl ethyl ketone or methyl isobutyl ketone, or a dialkylformamide, eg. dimethylformamide or diethylformamide, or dimethylsulfoxide or hexamethylphosphorotriamide, or a mixture of the said solvents. The reaction is advantageously accelerated, or completed, by heating, for example at 40°–120° C., preferably 80°–100° C. Amongst the solvents, the lower aliphatic ketones, dialkylformamides or dimethylsulfoxide are preferred.

The compounds of the formula (I), according to the invention, possess a chirality center at carbon atom 2 of the aliphatic side chain and are obtained as racemates, which can be separated into the optically active antipodes by conventional methods, for example by forming diastereomeric salts with optically active auxiliary acids, such as dibenzoyltartaric acid, camphor-10-sulfonic acid, ditoluyltartaric acid or 3-bromo-camphor-8-sulfonic acid.

If desired, the novel compounds obtained are converted to acid addition salts with a physiologically acceptable acid. Examples of suitable conventional physiologically acceptable organic or inorganic acids are hydrochloric acid, hydrobromic acid, phosphoric acid or sulfuric acid amongst inorganic acids and oxalic acid, maleic acid, fumaric acid, lactic acid, tartaric acid, malic acid, citric acid, salicylic acid, adipic acid or benzoic acid amongst organic acids; other acids may be found in Fortschritte der Arzneimittelforschung, volume 10, pages 224–225, Birkhäuser Verlag, Basel and Stuttgart, 1966, or in J. Pharm. Sci., 66 (1977), 1–5.

The acid addition salts are as a rule obtained in the conventional manner by mixing the free base or a solution thereof with the corresponding acid or a solution thereof in an organic solvent, for example a lower alcohol, eg. methanol, ethanol or propanol, or a lower ketone, eg. acetone, methyl ethyl ketone or methyl isobutyl ketone, or an ether, eg. diethyl ether, tetrahydrofuran or dioxane. To achieve better formation of crystals, mixtures of the said solvents may also be used. Furthermore, pharmaceutically acceptable aqueous solutions of acid addition compounds of the aminopropanol derivatives of the general formula (I) can be prepared by dissolving a free base of the general formula (I) in an aqueous salt solution.

The compounds according to the invention, and their physiologically acceptable acid addition salts, exhibit valuable pharmacological properties and can be used in cases of cardiac and circulatory disorders. Because of their $\beta$-sympatholytic action they are suitable for the treatment of coronary heart disease, of hypertonia and of cardiac arrhythmias. Regarding the use, action and properties of $\beta$-blocking agents, reference may be made, for example, to C. T. Dollery et al., Clinical Pharmacology and Therapeutics, 10 (1969), No. 6, 765–799, and the literature references given there.

The $\beta$-sympatholytic action was tested on rats, in comparison with the known $\beta$-sympatholytic agent propanolol (1-(isopropylamino)-1-naphthyloxy-2-propanol.HCl). The following methods were used for this purpose:

1. $\beta_1$-sympatholytic action

Isoproterenol (0.1 µg/kg, given intravenously) in pithed rats (Sprague-Dawley, Mus rattus; weight 230–280 g) causes increases in pulse rate of, on average, 45%. $\beta$-Sympatholytic agents inhibit such tachycardia. Isoproterenol was administered before, and 5 minutes after, the intravenous administration of the test substances. Linear relationships are found between the logarithms of the administered doses (mg/kg) of the test substances and the inhibition of the isoproterenol-induced tachycardia (%). From these relationships, the ED 50% is determined as the dose which inhibits the isoproterenol-induced tachycardia by 50%.

2. Acute toxicity

The acute toxicity was determined on groups of 10 female NMRI mice, weight 19–27 g, with intraperitoneal administration. The LD 50 was calculated (by Probit analysis) as the dose after which 50% of the animals died within 24 hours.

Table 1 shows that the pharmacotherapeutically important $\beta_1$-sympatholytic activity of the compounds according to the invention is 5.6 times greater (Example 1) or 3.2 times greater (Example 2) than that of the comparative substance propranolol. The therapeutic range, expressed as the quotient of the 50% lethal dose (LD 50) and the $\beta_1$-blocking dose (ED 50%) is 4 times greater (Example 2) or 7 times greater (Example 1) than that of propranolol.

TABLE 1

| Compound | $\beta_1$-sympatholytic action[1] ED 50%[2] | R.A.[3] | Acute toxicity LD 50[4] | Therapeutic range[5] absolute | relative[6] |
|---|---|---|---|---|---|
| Propranolol | 0.0127 | 1.00 | 108 | 111 | 1.00 |

TABLE 1-continued

| Compound | $\beta_1$-sympatholytic action[1] ED 50%[2] | R.A.[3] | Acute toxicity LD 50[4] | Therapeutic range[5] absolute | relative[6] |
|---|---|---|---|---|---|
| Example 1 | 0.00227 | 5.59 | 165 | 767 | 6.91 |
| Example 2 | 0.004 | 3.18 | 97.2 | 452 | 4.07 |

[1] Inhibition of isoproterenol-induced tachycardia in pithed rats. Intravenous administration
[2] Dose which inhibits the isoproterenol-induced tachycardia by 50%
[3] Relative activity. Propranolol = 1.00
[4] Mice. Intraperitoneal administration
[5] $\frac{LD\ 50}{ED\ 50\%}$
[6] Propranolol = 1.00

Accordingly, the present invention also relates to the therapeutic agents or formulations which in addition to conventional excipients and diluents contain a compound of the formula (I) as the active ingredient, and to the use of the novel compounds in the treatment of cardiac and circulatory disorders.

The therapeutic agents and formulations are prepared in the conventional manner by employing the conventional excipients or diluents and the conventional pharmacological assistants, in accordance with the desired administration route, and in a suitable dosage.

The preferred formulations are forms suitable for oral administration. Examples of such forms are tablets, film tablets, dragees, capsules, pills, powders, solutions, suspensions or depot forms.

Of course, parenteral formulations, such as injection solutions, may also be used. A further example of suitable formulations is suppositories.

For man, a suitable single dose of the compounds according to the invention is from 1 to 100 mg, preferably from 2 to 50 mg.

Compounds to be singled out particularly by virtue of their activity are 2-[2-(3-tert.-butylamino-2-hydroxypropoxy)-phenyl]-pyrrole and 2-[2-(3-isopropylamino-2-hydroxypropoxy)-phenyl]-pyrrole.

Further examples to be mentioned are: 2-[2-(3-cyclopropylamino-2-hydroxypropoxy)-phenyl]-pyrrole, 2-[2-(3-sec.-butylamino-2-hydroxypropoxy)-phenyl]-pyrrole, 2-[2-[3-(3-methyl-but-1-yn-3-yl-amino)-2-hydroxypropoxy]-phenyl]-pyrrole and 2-[2-[3-(but-1-yn-3-yl-amino)-2-hydroxy-propoxy]-phenyl]-pyrrole.

The Examples which follow illustrate the invention.

I. PREPARATION OF STARTING COMPOUNDS 1. o-Benzyloxybenzoic acid allylamide (A) 30 g of methyl o-benzyloxybenzoate and 15 ml of allylamine are refluxed for 7 days. The residue is recrystallized from ether at −25° C.

Yield: 17.2 g, corresponding to 52% of theory; melting point 48° C.

(B) 4.9 g (20 millimoles) of O-benzylsalicyclic acid chloride in 10 ml of dioxane are introduced slowly into an ice-cooled solution of 1.7 g (30 millimoles) of allylamine and 4 g of sodium bicarbonate in 100 ml of water, and the mixture is stirred overnight. The product is filtered off and recrystallized as under (A).

Yield: 4.3 g, corresponding to 80% of theory.

2. 2-(o-Benzyloxyphenyl)-pyrrole 2.7 g (10 millimoles) of o-benzyloxybenzoic acid allylamide in 20 ml of a 20% strength by weight solution of phosgene and toluene are stirred, in the presence of 2 drops of dimethylformamide, at room temperature overnight. The residue which remains after distilling off the toluene under reduced pressure at 40° C. bath temperature is taken up in 30 ml of tetrahydrofuran and the solution is filtered through glass wool and is introduced, in the course of 45 minutes, into an ice-cooled solution of 4.0 g (30 millimoles) of potassium tert.-butylate in 60 ml of a 1:1 (by volume) mixture of tetrahydrofuran and benzene, under argon as a protective gas. 10 minutes after completion of the addition, the solvent is distilled off under reduced pressure, the residue is partitioned between methylene chloride and water, and the aqueous phase is extracted twice with methylene chloride.

The organic phases are combined, dried over sodium sulfate and evaporated and the residue is chromatographed on a short silica gel column (30×2 cm) using carbon tetrachloride as the eluant. The oil which remains after concentrating the eluates is recrystallized from methanol.

Yield: 1.4 g, corresponding to 56% of theory; melting point 72° C.

Analysis: $C_{17}H_{15}NO$; 249.3. Calculated: 81.90 C; 6.06 H; 5.62 N. Found: 81.76 C; 6.00 H; 5.45 N.

3. 2-(o-Hydroxyphenyl)-pyrrole 150 mg of 10% strength palladium-on-charcoal catalyst are added to 1.5 g (6 millimoles) of 2-(o-benzyloxyphenyl)-pyrrole in 30 ml of methanol and hydrogenation is carried out under slightly superatmospheric pressure. The residue which remains after separating off the catalyst and evaporating the solution is recrystallized from a mixture of toluene and petroleum ether (boiling range 40°-60° C.). The yield of 0.8 g corresponds to 84% of theory; melting point 100°-101° C.

Analysis: $C_{10}H_9NO$; 159.19. Calculated: 75.45 C; 5.70 H; 8.80 N. Found: 75.40 C; 5.70 H; 8.76 N.

4. 2-[2-(2,3-Epoxypropoxy)-phenyl]-pyrrole 7.0 g of 2-(o-hydroxyphenyl)-pyrrole, 7.3 g of epibromohydrin and 11.4 g of dry potassium carbonate in 50 ml of acetone are refluxed for 7 hours. After the mixture has cooled, it is filtered and the filter residue is washed with acetone. The combined filtrates are freed from the solvent by distillation. The residue is chromatographed twice on silica gel, using methylene chloride as the eluant, and gives 4.6 g (48% of theory) of 2-[2-(2,3-epoxypropoxy)-phenyl]-pyrrole as a colorless oil.

$^1$H-NMR spectrum (CDCl$_3$, TMS as internal standard): $\delta$=2.65 (m, 2H); 3.25–3.6 (m, 1H); 4.23 (m, 2H); 6.28 (m, 1H); 6.68 (m, 5H); 7.59 (m, 1H); 10.0 (broad, 1H).

II. PREPARATION OF COMPOUNDS ACCORDING TO THE INVENTION

EXAMPLE 1

1.5 g of 2-[2-(2,3-epoxypropoxy)-phenyl]-pyrrole and 1 ml of tert.-butylamine in 5 ml of ethanol are left to stand overnight and the solvent and excess amine are then distilled off. The waxy residue is dissolved in a small amount of ethanol and a solution of fumaric acid in ether is added dropwise. The 2-[2-(3-tert.-butylamino-2-hydroxypropoxy)-phenyl]-pyrrole fumarate which has precipitated is filtered off, washed with dry ether and then dried.

Yield: 1.8 g (75% of theory) of melting point 197°-198° C.

$C_{19}H_{26}O_4N_2$: (346). Calculated: 65.8 C; 7.6 H; 8.1 N. Found: 65.3 C; 7.5 H; 7.9 N.

EXAMPLE 2

1.5 g of 2-[2-(2,3-epoxypropoxy)-phenyl]-pyrrole and 3 ml of isopropylamine are reacted by the method described in Example 1. After recrystallization from a 1:1 methanol-ethanol mixture, 0.7 g (30% of theory) of 2-[2-(3-isopropylamino-2-hydroxypropoxy)-phenyl]-pyrrole fumarate hemihydrate of melting point 176°-177° C. are obtained.

$C_{18}H_{24}O_4N_2 \cdot \frac{1}{2}H_2O$: (341). Calculated: 63.3 C; 7.3 H; 8.21 N. Found: 63.4 C; 7.2 H; 8.1 N.

Examples of formulations prepared in the conventional manner:

| 1. Tablets: | |
| --- | --- |
| (a) An active ingredient of the formula I | 5 mg |
| Lactose | 200 mg |
| Methylcellulose | 15 mg |
| Corn Starch | 50 mg |
| Talc | 11 mg |
| Magnesium stearate | 4 mg |
| | 285 mg |
| (b) An active ingredient of the formula I | 20 mg |
| Lactose | 178 |
| Avicel | 80 mg |
| Polywachs 6000 (polyethylene oxide) | 20 mg |
| Magnesium stearate | 2 mg |
| | 300 mg |
| (c) An active ingredient of the formula I | 50 mg |
| Polyvinylpyrrolidone (mean molecular weight 25,000) | 170 mg |
| Polyethylene gylcol (mean molecular weight 4,000) | 14 mg |
| Hydroxypropylmethylcellulose | 40 mg |
| Talc | 4 mg |
| Magnesium stearagte | 2 mg |
| | 280 mg |

The active ingredient is moistened with a 10% strength aqueous solution of polyvinylpyrrolidone, forced through a sieve of 1.0 mm mesh width, and dried at 50° C. The granules thus obtained are mixed with the polyethylene glycol (mean molecular weight 4,000), hydroxpropylmethylcellulose, talc and magnesium stearate and the mixture is pressed to give tablets each weighing 280 mg.

| 2. Example of dragees: | |
| --- | --- |
| An active ingredient of the formula I | 60 mg |
| Lactose | 90 mg |
| Corn starch | 60 mg |
| Polyvinylpryrrolidone | 6 mg |
| Magnesium stearate | 1 mg |
| | 217 mg |

The mixture of the active ingredient with lactose and corn starch is moistened with an 8% strength aqueous solution of the polyvinylpyrrolidone and granulated by forcing through a 1.5 mm mesh width sieve, after which it is dried at 50° C. and again forced through a 1.5 mm mesh width sieve. The granules thus obtained are mixed with magnesium stearate and the mixture is pressed to form dragee cores. The cores obtained are coated in the conventional manner with a shell consisting essentially of sugar and talc.

| 3. Capsule formulation: | |
| --- | --- |
| An active ingredient of the formula I | 5.0 mg |
| Magnesium stearate | 2.9 mg |

| 3. Capsule formulation: | |
|---|---|
| Lactose | 19.3 mg |

| 4. Injection solution: | |
|---|---|
| An active ingredient of the formula I | 10 mg |
| Sodium chloride | 9 mg |
| Distilled water, sufficient to give 1.0 ml | |

We claim:

1. A compound of the formula (I)

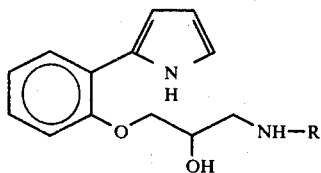

where R is alkyl of 3 to 6 carbon atoms which is branched at the carbon in the α-position to the nitrogen or an alkyl of 3 to 6 carbon atoms which is branched at the carbon in the α-position to the nitrogen and is substituted by an alkoxy group of 1 to 3 carbon atoms, and its physiologically acceptable acid addition salts.

2. 2-[2-(3-tert.-Butylamino-2-hydroxypropoxy)-phenyl]-pyrrole.

3. 2-[2-(3-Isopropylamino-2-hydroxypropoxy)-phenyl]-pyrrole.

4. A therapeutic agent for the treatment of cardiac and circulatory disorders which comprises a therapeutically effective amount of a compound as set forth in claim 1, or a physiologically acceptable acid addition salt thereof, together with conventional excipients and diluents.

5. The therapeutic agent of claim 4, which comprises 2-[2-(3-tert.-butylamino-2-hydroxypropoxy)-phenyl]-pyrrole or a physiologically acceptable acid addition salt thereof together with conventional excipients and diluents.

6. The therapeutic agent of claim 4, which comprises 2-[2-(3-isopropylamino-2-hydroxypropoxy)-phenyl]-pyrrole or a physiologically acceptable acid addition salt thereof together with conventional excipients and diluents.

* * * * *